United States Patent [19]

Larson

[11] 4,136,554

[45] Jan. 30, 1979

[54] TESTER FOR INFLATED ITEMS

[75] Inventor: Raymond B. Larson, South Bend, Ind.

[73] Assignee: Wells Electronics, Inc., South Bend, Ind.

[21] Appl. No.: 847,228

[22] Filed: Oct. 31, 1977

[51] Int. Cl.² ............................................. G01N 3/48
[52] U.S. Cl. ........................................................ 73/81
[58] Field of Search ........................ 73/78, 81, 85, 52; 273/61 D

[56] References Cited

U.S. PATENT DOCUMENTS

| | | | |
|---|---|---|---|
| 1,549,115 | 8/1925 | Hancock | 73/81 |
| 1,802,685 | 4/1931 | Trier | 73/81 |
| 1,875,862 | 9/1932 | Fair | 73/81 |
| 2,039,337 | 5/1936 | Nolan | 73/81 X |
| 2,358,370 | 9/1944 | Williams | 73/81 |
| 2,384,437 | 9/1945 | Boynton | 73/81 |
| 2,648,977 | 8/1953 | Mills | 73/81 X |
| 2,807,161 | 9/1957 | Wirant | 73/81 |
| 3,889,807 | 6/1975 | Feinberg et al. | 273/61 D X |

*Primary Examiner*—Charles Gorenstein
*Attorney, Agent, or Firm*—Oltsch, Knoblock & Hall

[57] ABSTRACT

A device for testing inflated objects such as tennis balls, wherein a housing contains a testing chamber in which the inflated object is compressed in a testing operation to an extent correlated to its inflation pressure.

Measuring means calibrated to indicate inflation pressure are carried by the housing and include a sensing member contacting the object being tested and displaced in said testing operation from a normal position to an extent dependent upon the inflation pressure of said object.

9 Claims, 8 Drawing Figures

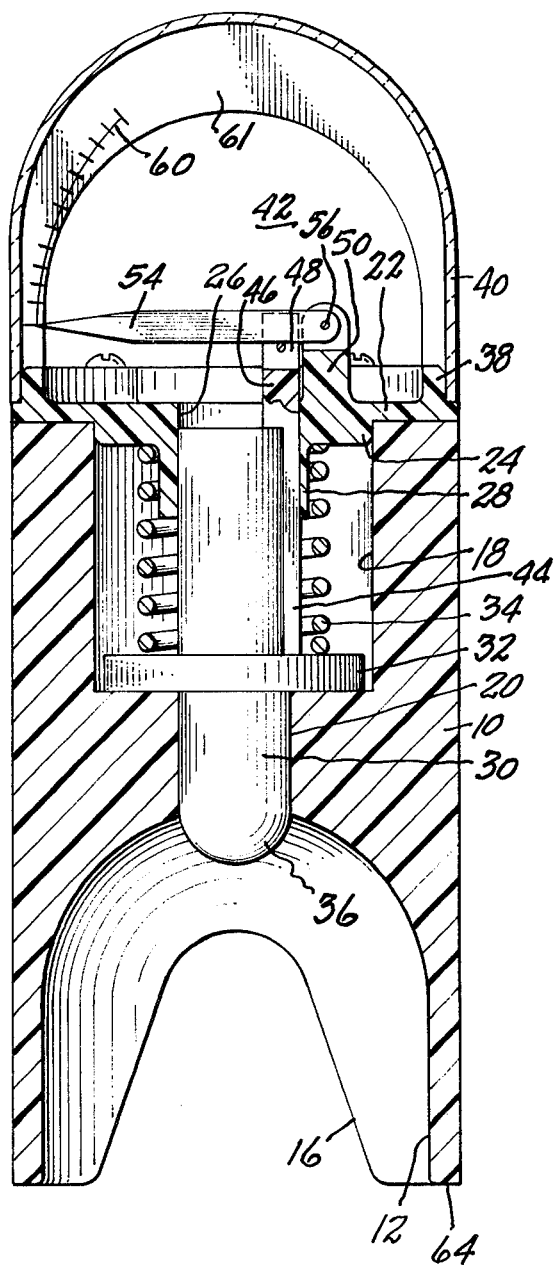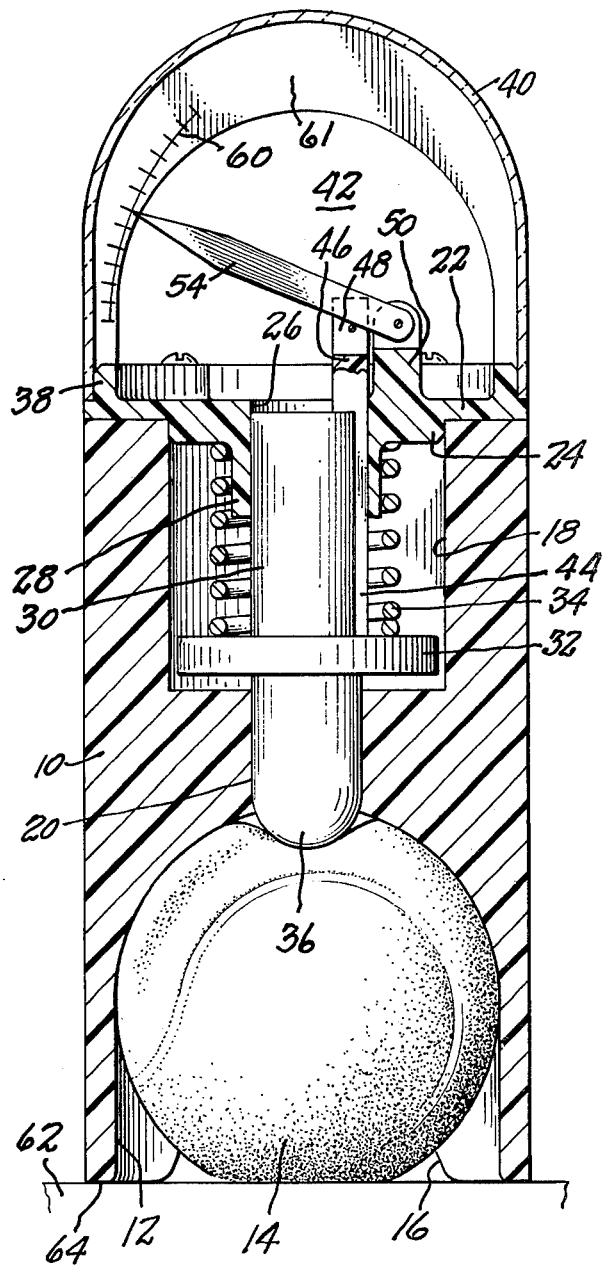

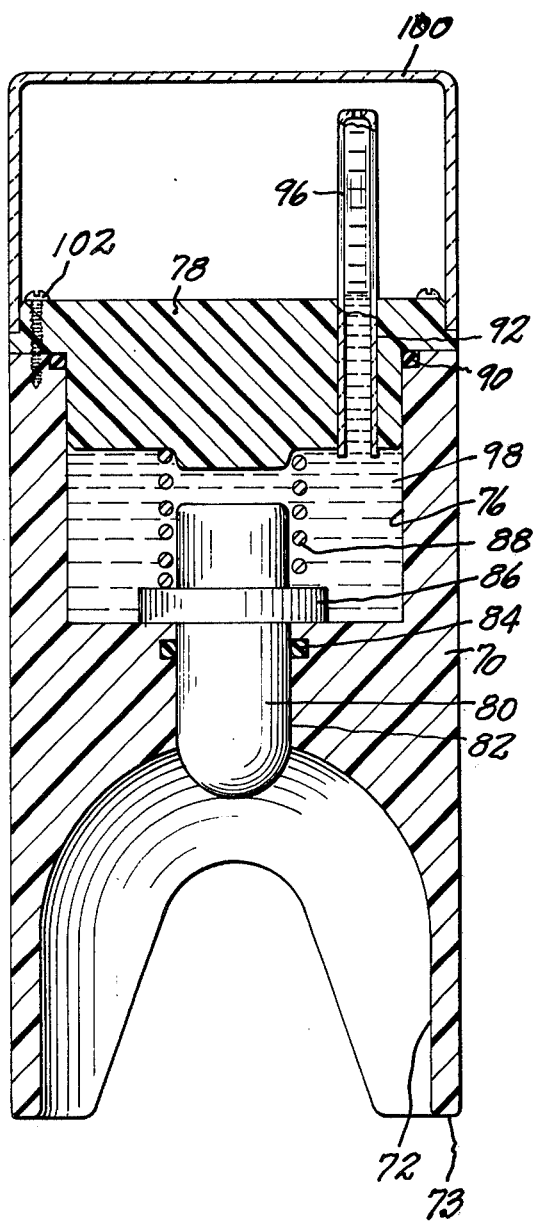
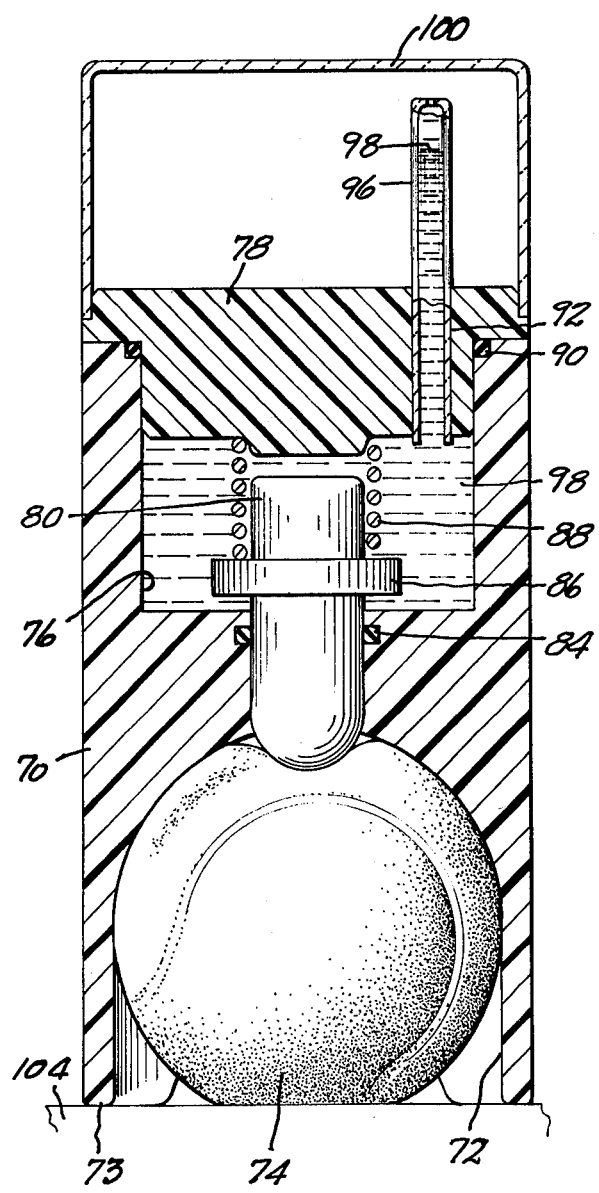

TESTER FOR INFLATED ITEMS

SUMMARY OF THE INVENTION

This invention relates to improvements in testers for inflated items and more particularly to devices for testing the pressure of tennis balls and racquet balls.

Inflated game balls such as tennis balls and racquet balls are commonly sold in sealed cans designed to retain the pressure injected therein by the manufacturer. Thus, a tennis ball which is removed from its sealed container is subject to loss of pressure when removed from the can, and particularly is subject to gradual loss of pressure as evidenced by loss of its bouncing properties as it is used in play. Professional players discard balls after playing a few games because the pressure in the balls has dropped below a selected value, usually below 12 psi. The rate at which tennis balls lose pressure varies so that there is no standard length of service which is applicable to all balls even as to the balls dispensed in the same sealed container.

Ball inflation is now determined by observing or comparing the bouncing properties of balls or by squeezing or "feeling" a ball in the palm of the hand of a player. Such bounce, feel and squeeze tests are unsatisfactory at best and obviously differ in interpretations by different people and depend upon the degree of experience and practice which a player or user possesses. Thus, there is a fine degree of difference between (a) balls which are acceptable for play, (b) those of lesser pressure but acceptable for use for practice only, and (c) those which are totally unacceptable due to low pressure, and different individuals have different standards so that different individuals testing the same ball may grade it differently.

The loss of pressure of inflated balls is a fact well known to tennis players and racquet ball players and various devices are available on the market designed to pressurize a ball, such as devices in which a ball is subjected to air pressure. Such devices operate on the premise that the existence of high air pressure around a ball will, through osmosis, build up the pressure within the ball. Most of these devices are ineffective because the average user does not recognize that a long period of time, such as two or three weeks, is required for the balls to absorb the higher pressure in the pressurizer. Also, most of these products do not actually measure the pressure in the ball. A few devices are available which act to inflate the ball and to measure the pressure thereof, but such devices heretofore have been too expensive for the average tennis player. Another type of device utilizes an aerosol can containing pressurized air and a sealant, and is provided with a hollow needle which pierces the ball and inflates it, relying upon the sealant to reseal the ball when the needle is withdrawn. Devices of this character include no guide for pressure measurement and permit over-pressurizing the ball to an extent rendering it unsuitable for play.

It is the primary object of this invention to provide a device by which an inflated item can be tested quickly to ascertain the pressure thereof and determine whether the pressure therein falls within accepted limits.

A further object is to provide a device of this character which can be produced economically so that it can be sold at a price which the average tennis player is able and willing to pay.

A further object is to provide a tester of this character which can be used quickly by a simple manipulation which provides a quick pressure indication, so that it can be used during the play of a game without objectionably delaying the game.

Other objects will become apparent from the following specifications.

BRIEF DESCRIPTION OF THE DRAWINGS

In the drawings.

FIG. 5 is a vertical sectional view of the tester in idle or normal position.

FIG. 6 is a vertical sectional view taken along line 5—5 of FIG. 4 and illustrating the test position of the device.

FIG. 7 is a sectional view illustrating a modified embodiment of the invention.

FIG. 8 is a sectional view similar to FIG. 7 illustrating the device of FIG. 7 in its test position.

DESCRIPTION OF THE PREFERRED EMBODIMENT

The device comprises a housing having a chamber to receive the item being tested and into which extends a spring urged plunger which controls a pressure indicating device visible by the user. The chamber for receiving the test item is so dimensioned that upon closing of the chamber by the user, as by pressing an open end thereof against a closure or abutment member, the test item is deformed and displaces the plunger against the action of its controlling spring to actuate the indicator in proportion to the extend of deformation of the test item as determined by its contained pressure.

Figure 1:
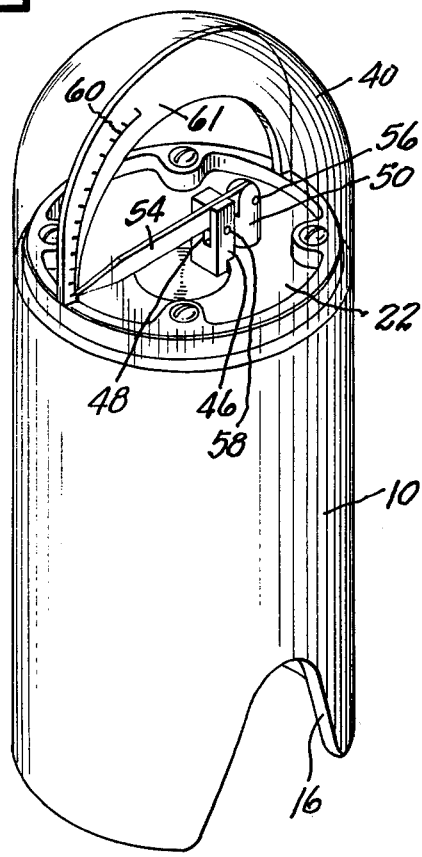
FIG. 1 is a perspective view of one embodiment of the invention.
Figure 2:
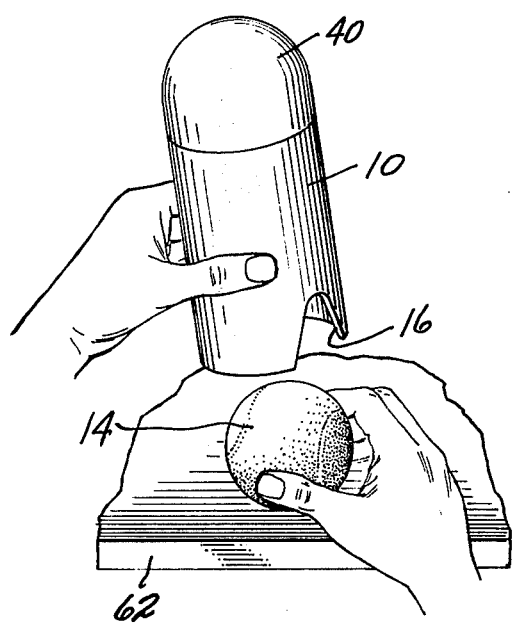
FIG. 2 is a perspective view illustrating commencement of use of the tester.
Figure 4:
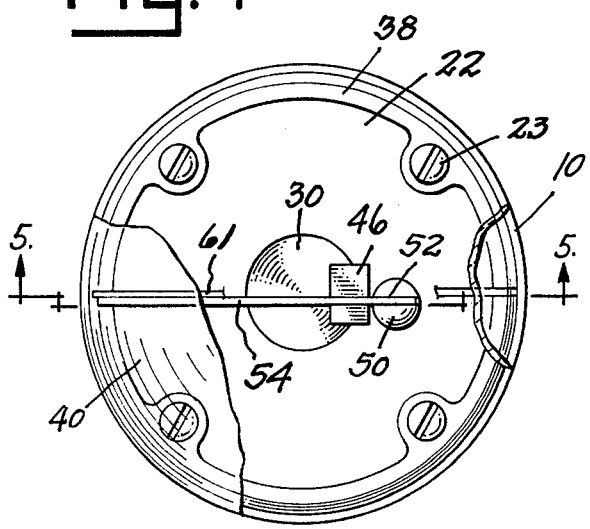
FIG. 4 is a top plan view of the device with parts broken away.
Figure 3:
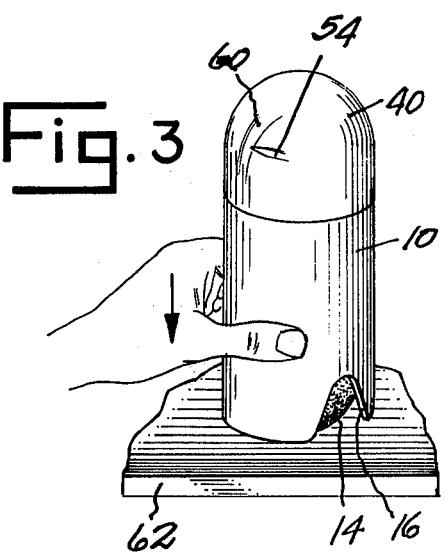
FIG. 3 is a perspective view illustrating the test position of the tester.

Referring to the drawings and particularly FIGS. 1-6 inclusive which illustrate one embodiment of the invention, the numeral 10 designates a housing which is preferably molded from a rigid synthetic material or metal. Housing 10 has a cavity 12 open at one end thereof which is preferably circular when the device is used to test a spherical member. The cavity has a diameter or shape to receive and position centrally therein a ball or other inflated member 14 and has a depth not greater than and preferably slightly less than the diameter of the ball 14. The walls of the cavity 12 are preferably interrupted at recesses, notches or openings 16, preferably at opposite sides thereof. A second cavity 18 is open at the opposite end of housing 10, the same preferably being cylindrical and concentric with the housing. A central passage 20 is formed in the housing 10 and is open at the cavities 12 and 18 at its opposite ends. A plate 22 is secured on the end of the housing at which the second cavity 18 opens by screws 23. Plate 22 preferably is provided with a concentric thickened portion 24 of a size to seat in the open end of the cavity 18 and thus properly orient the plate 22 to the housing 10. The plate 22 has a central axial bore 26 therein, axially aligned with the passage 20. Plate 22 is also preferably provided with a central tubular part 28 which projects downwardly into the cavity 18.

The tubular part 28 of the plate 22 and the passage 20 of the housing cooperate to slidably receive and to guide a plunger 30 having an enlarged disk portion 32 intermediate its ends which normally seats on the bottom of the cavity 18 in which it has clearance. A coil spring 34 encircles the plunger 30 and the central tubular part 28 of the plate 22, the same bearing at its lower end upon the disk 32 and at its upper end against the portion 24 of the plate 22. The lowermost end of the plunger 30, i.e. that portion below the disk 32, is of a length greater than the length of the passage 20, is slidable in passage 20, and preferably terminates in a rounded part-sperical end portion 36 which projects into the cavity 12, when the disk 32 is seated at the bottom of the cavity 18, to a predetermined extent, such as the extent of projection illustrated in FIG. 5. The plate 22 preferably includes an upperwardly projecting rib 38, preferably circular. A transparent inverted cup shaped member or dome 40 is mounted upon the margin of the plate 22 as positioned by the rib 38 and forms an upper chamber 42 of the device.

The upper portion of the plunger 30 above the disk 32 is preferably provided with a longitudinal rib 44 which is preferably received in and guided by a groove in the plate 22 and its central tubular part 28. A part 46 projects upwardly and endwise from the plunger 30 and rib 44 and has a vertical slot 48 in its upper end. Plate 22 is provided with an upper projection 50 adjacent to the slot in tubular part 28 which guides the plunger projection 46, and said projection 50 has a vertical slot 52 therein which is aligned with slot 48 in plunger 46. A pointer or indicator 54 is pivoted at 56 at an end thereof which fits in the slot 52, said pointer passing through the slot 48 in the plunger projection 46 and preferably bearing upon a cross pin 58 extending across the slot 48 of the plunger projection. The free or indicating end of the pointer 54 is juxtaposed to a scale 60 which may be embossed or etched in the dome 40 or upon a member 61 enclosed in selected position within the transparent dome member 40. The parts are so proportioned that the pointer 50 will preferably be substantially horizontal to indicate the low point on the scale 60 when the plunger is in its normal inoperative position at which the disk 32 seats upon the bottom of the cavity 18 as illustrated in FIG. 5. The scale 60 will be of such length that the pointer will reach the high point thereof only when the maximum expected pressure of an inflated member being tested is encountered in use.

In the use of the device, the ball 14 is supported upon the surface of a rigid member 62 which preferably is substantially flat. The housing 10 of the tester is then applied around the ball at the cavity 12 as illustrated in FIG. 6, the notches 16 accommodating the application of the housing around the ball. The user then applies pressure to the housing 10 to bring the lower end edge 64 of the housing into contact with the member 62 and maintains the housing in that position while the position of the pointer 54 relative to the scale 60 is observed. The action of lowering the housing into contact with the member 62 while a ball 14 is confined within the cavity 12 results in compression of the ball to an extent determined by the internal pressure within the ball. As the ball is compressed, the plunger 30 is displaced upwardly in proportion to the internal pressure of the ball to unseat the plunger disk 32, compress the spring 34, and elevate the plunger extension 46 and the pin 56 to thereby tilt the pointer 54 upwardly, as seen in FIG. 6. The scale 60 may be so calibrated as to indicate the pressure of the ball within (a) a selected range of acceptable playing pressure which may be indicated at the upper end of the scale 60, (b) a lesser pressure but sufficient for use of the ball during practice as indicated in an intermediate part of the scale, and (c) an unacceptable pressure at the lower part of the scale. The scale may have any suitable means (not shown) associated therewith to indicate the range at which a ball is tested, such as a band of color at the upper end of the scale indicating a ball which is playable, a second band of color at the intermediate part of the scale indicating a ball unacceptable for play by usable for practice, and a band of a third color at the lower end of the scale indicating an unplayable ball.

It will be evident that the time required to test a ball and determine its pressure condition and its gradation as between playable condition and practice condition and unacceptable condition is very short, so that the use of the tester during a game to test the balls in play as to their acceptability is so short that no objectionable delay of the game occurs.

Another embodiment of the invention is illustrated in FIG. 7 and 8. In this construction, a housing 70 has an open ended test chamber 72 for the ball 74 to be tested and an upper cavity 76 which is spanned and closed by an upper closure plate 78. A plunger 80 is slidably received in a passage 82 which is preferably interrupted by an annular groove housing a sealing ring 84. Plunger 80 has an enlarged disk 86 intermediate its ends which is normally pressed against the bottom of the chamber or cavity 76 by a coil spring 88. A suitable seal 90, such as a ring seated in a groove, extends around the upper end of the housing and in contact with the upper closure plate 78 to insure that a liquid 98 contained in the upper cavity 76 cannot leak therefrom similarly to the seal 84 provided to resist leakage around the plunger 80.

Closure plate 78 has a passage 92 therethrough displaced from the center thereof and from the spring 88. A transparent tube 94 is mounted in passage 92 and projects above plate 78. Tube 94 has graduations 96 along the length of its projecting portion by means of which the level of liquid 98 in the tube, which liquid is preferably colored, can be observed and measured. A transparent closure or cover 100 is mounted on the upper end of the device. The upper closure plate 78 is preferably anchored to the housing, as by anchor screws 102, and the transparent cover is suitably mounted upon and partially surrounds the upper closure plate.

The use of the device of this embodiment is substantially the same as use of the first embodiment. The device is placed to enclose ball 74 to be tested within the test chamber 72, followed by application and maintenance of pressure endwise upon the housing to force its end edge 73 against the surface of a supporting member 104 so as to compress the ball 74 and cause it to be indented by the plunger 80 which is displaced endwise in the housing to an extent determined by the amount of pressure contained within the test ball 74. The lower end of the tube 94 is open to the cavity 76 and is normally filled with liquid to a level at or adjacent the top of the upper closure plate 78. As the plunger 80 is displaced upwardly by the resistance to compression provided by the test ball 74, liquid 98 will be displaced from the chamber 76 into the upper portion of the tube 94 at which its liquid level can be observed.

While the preferred embodiments of the invention have been illustrated and described it will be understood that changes in the construction may be made within the scope of the appended claims without departing from the spirit of the invention.

What I claim is:

1. A device for testing the pressure of inflated objects comprising
    a housing having a test chamber formed in one end thereof and adapted to receive an inflated object to be tested, said end adapted to bear upon a supporting member, the depth of said chamber being not greater than a dimension of said object,
    a spring pressed plunger slidable in said housing and normally positioned to project into said test chamber toward said supporting member, and
    means for measuring the displacement of said plunger from normal position incident to compressive deformation of said object within the confines of said test chamber between said plunger and said supporting member when the chambered end of said housing engages said supporting member.

2. A device as defined in claim 1, wherein said test chamber is open to freely receive said object, is of a size to normally receive a selected portion of the object and accommodates reception of said compressively deformed inflated object therein as the volume of said chamber is reduced to a predetermined extent.

3. A device as defined in claim 1, wherein said measuring means includes an indicator pivoted to said housing and shifted by movement of said plunger.

4. A device as defined in claim 1, wherein said measuring means includes an indicator pivoted to said housing and engaged and shiftable by said plunger, and a graduated pressure indicating scale covered by said housing positioned adjacent the free end of said indicator.

5. A device as defined in claim 1, wherein said plunger is slotted to receive and guide a portion of said indicator.

6. A device as defined in claim 1, and
    a transparent member carried by said housing and enclosing said measuring means.

7. A device as defined in claim 1, wherein
    said measuring means includes indicia correlated to and providing readings of different ranges of pressure of an inflated object being tested.

8. A device as defined in claim 1, wherein said housing includes a liquid containing chamber into which a portion of said plunger normally projects, and
    said measuring means includes liquid level means for indicating displacement of liquid incident to movement of said plunger in said liquid chamber.

9. A device for testing the pressure of inflated objects comprising
    a housing having a test chamber adapted to receive only a part of an inflated object and an open portion adapted to engage closing means to close said chamber and having a testing condition when said chamber is closed which causes compression of said object to an extent correlated to the inflation pressure of said object
    a spring pressed plunger slidable and guided in said housing and normally positioned to project into said test chamber in the direction in which the object is compressed, said plunger being slidable from a predetermined position as it is displaced in said testing condition by the object being tested, and
    measuring means responsive to the displacement of said plunger and in shiftable relation to a scale calibrated to indicate the inflation pressure of the object being tested.

* * * * *